US011026653B2

(12) United States Patent
Amr et al.

(10) Patent No.: US 11,026,653 B2
(45) Date of Patent: Jun. 8, 2021

(54) METHOD AND APPARATUS FOR CALIBRATING AN X-RAY SYSTEM

(71) Applicant: Fraunhofer-Gesellschaft zur Foerderung der angewandten Forschung e.V., Munich (DE)

(72) Inventors: Mahmoud Amr, Fuerth (DE); Tobias Schoen, Nuremberg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 256 days.

(21) Appl. No.: 16/261,049

(22) Filed: Jan. 29, 2019

(65) Prior Publication Data
US 2019/0159748 A1 May 30, 2019

Related U.S. Application Data

(63) Continuation of application No. PCT/EP2017/069193, filed on Jul. 28, 2017.

(30) Foreign Application Priority Data

Jul. 29, 2016 (DE) ..................... 10 2016 214 062.0

(51) Int. Cl.
A61B 6/00 (2006.01)
G01N 23/046 (2018.01)
A61B 6/03 (2006.01)

(52) U.S. Cl.
CPC ............ *A61B 6/584* (2013.01); *A61B 6/032* (2013.01); *G01N 23/046* (2013.01)

(58) Field of Classification Search
CPC ....... A61B 6/584; A61B 6/032; G01N 23/046
See application file for complete search history.

(56) References Cited

U.S. PATENT DOCUMENTS

2012/0201352 A1\* 8/2012 Dennerlein .......... A61B 6/4452
378/62

FOREIGN PATENT DOCUMENTS

DE 102005033187 A1 1/2007
DE 102007056276 A1 6/2009
(Continued)

OTHER PUBLICATIONS

Cheng, Frank Shaopeng, "Calibration of robot reference frames for enhanced robot positioning accuracy", Robot Manipulators, Marco Ceccarelli (Ed.), ISBN: 978-953-7619-06-0, InTech, www.intechopen.com/books/robot_manipulators/calibration_of_robot_reference_frames_for_enhanced_robot_positioning_accuracy, Sep. 1, 2008, pp. 95-112.

(Continued)

*Primary Examiner* — Courtney D Thomas
(74) *Attorney, Agent, or Firm* — Michael A. Glenn; Perkins Coie LLP

(57) ABSTRACT

A method for calibrating an X-ray system having a radiation source and a radiation detector has the steps of establishing a kinematic model for at least one position, setting starting values, calibrating and solving a system of equations by means of minimizing. The system of equations is set up by the respective established kinematic model of the X-ray system, wherein the system of equations has respective sets of kinematic parameters for each position, and parameters to be calibrated which are usually equal over all the positions. In the step of setting the starting values, the parameters to be calibrated are set and, based on these, in the step of calibrating, at least one recording is taken by means of calibration bodies so that a comparison of the measuring results to respective references results in an error measure. This error measure is minimized when solving the system of equations.

26 Claims, 4 Drawing Sheets

(56) References Cited

FOREIGN PATENT DOCUMENTS

WO    2012007036 A1    1/2012
WO    2015051468 A1    4/2015

OTHER PUBLICATIONS

Heyer, Torsten, et al., "Camera Calibration for Reliable Object Manipulation in Care-Providing Robot FRIEND", Technical report, Institute of Automation (IAT), University of Bremen, Jun. 2010, pp. 1-6.

Hu, Zhanli, et al., "Geometric Calibration of a Micro-CT System and Performance for Insect Imaging", IEEE Transactions on Information Technology in Biomedicine, vol. 15, No. 4, Jul. 2011, pp. 655-660.

Mery, Domingo, et al., "Geometric Calibration of a X-ray Testing System", Technische Universität Berlin. NDT.net—vol. 7 No. 03, Mar. 2002, pp. 1-7.

Robo-Technology GMBH, "UltraCal Laser-based Robot Calibration System", http://www.robotechnology.de/UltraCal_V5.pdf, pp. 1-2.

Stopp, Fabian, et al., "A Geometric Calibration Method for an Open Cone-Beam CT System", The 12th International Meeting on Fully Three-Dimensional Image Reconstruction in Radiology and Nuclear Medicine, Charité Universitätsmedizin Berlin, Jun. 2013, pp. 106-109.

Sun, Yi, et al., "A Calibration Method for Misaligned Scanner Geometry in Cone-beam Computed Tomography", Technische Universität Berlin, NDT & E International 39(6), Sep. 2006, pp. 499-513.

Thürauf, Sabine, et al., "Evaluation of a 9D-Position Measurement Method of C-Arm Based on X-Ray Projections", Proceedings of the Medical Image Computing and Computer-Assisted Intervention (MICCAI) Conference, 2015, Oct. 2015, pp. 1-10.

Wang, Wei, et al., "Calibration method of robot base frame using unit quaternion form", Technical report, Central Michigan University, Precision Engineering 41(3), Feb. 2015.

Wikipedia, "Robotics conventions", Https://en.wikipedia.org/w/index.php?title=Robotics_conventions, Jan. 4, 2014, pp. 1-4.

Yahui, Gan, et al., "Base frame calibration for coordinated industrial robots", Technical report, School of Automation, Southeast University, Nanjing, 210096, PR China, Robotics and Autonomous Systems 59, Apr. 20, 2011, pp. 563-570.

Yang, Kai, et al., "A geometric calibration method for cone beam CT systems", Med Phys; 33(6), Jun. 2006, pp. 1695-1706.

Zhao, Jintao, et al., "Geometric Parameters Estimation and Calibration in Cone-Beam Micro-CT", Sensors 2015, 15; doi:10.3390/s150922811, Sep. 9, 2015, pp. 22811-22825.

* cited by examiner

| q | d | a | α |
|---|---|---|---|
| $\theta_1$ | 0 | 0 | $-\pi/2$ |
| $\theta_2$ | 0 | 450 | 0 |
| $\theta_3$ | 0 | 0 | $\pi/2$ |
| $\theta_4$ | 450 | 0 | $-\pi/2$ |
| $\theta_5$ | 0 | 0 | $\pi/2$ |
| $\theta_6$ | 85 | 0 | 0 |

Fig. 2a

| q | d | a | α |
|---|---|---|---|
| d0 | d1 | d2 | d3 |
| $\theta_{12}$ | 85 | 0 | 0 |
| $\theta_{11}$ | 0 | 0 | $\pi/2$ |
| $\theta_{10}$ | 450 | 0 | $-\pi/2$ |
| $\theta_9$ | 0 | 0 | $\pi/2$ |
| $\theta_8$ | 0 | 450 | 0 |
| $\theta_7$ | 0 | 0 | $-\pi/2$ |
| b0 | b1 | b2 | b3 |
| $\theta_1$ | 0 | 0 | $-\pi/2$ |
| $\theta_2$ | 0 | 450 | 0 |
| $\theta_3$ | 0 | 0 | $\pi/2$ |
| $\theta_4$ | 450 | 0 | $-\pi/2$ |
| $\theta_5$ | 0 | 0 | $\pi/2$ |
| $\theta_6$ | 85 | 0 | 0 |
| s0 | s1 | s2 | s3 |

Fig. 2b

METHOD AND APPARATUS FOR CALIBRATING AN X-RAY SYSTEM

CROSS-REFERENCE TO RELATED APPLICATIONS

This application is a continuation of copending International Application No. PCT/EP2017/069193, filed Jul. 28, 2017, which is incorporated herein by reference in its entirety, and additionally claims priority from German Application No. 10 2016 214 062.0, filed Jul. 29, 2016, which is also incorporated herein by reference in its entirety.

BACKGROUND OF THE INVENTION

Embodiments of the present invention relate to a method and an apparatus for an X-ray-based calibration and adjustment of axis systems, like axis systems of an X-ray system or computer tomography system.

In computer tomography, an adjusted axis system and knowledge on the position of the focal spot and imaging or mapping plane relative to the axis systems are needed for recording and reconstructing data. In particular in robot-supported CT systems, this means major challenges for the precision in manufacturing and setting up the system. Consequently, the quantities are frequently determined after setting up the system using algorithms for calibration or correction.

Knowledge on the configuration of the axis system plays a particularly important role here. In laboratory systems for circle or helix CT, these are adjusted manually, which is frequently complicated, until a manually tested image quality in 2D and 3D is achieved. Replacing components, like an X-ray tube or detector, here frequently means re-adjusting the system. More complex systems having more complicated trajectories cannot be calibrated using classical approaches since the trajectory depends on too many degrees of freedom or the manipulators are freely positioned in space.

Current methods are usually based on fixed defined trajectories (like circle, helix), highly precise reference bodies and/or determine only limited degrees of freedom of the system (like detector misalignment in two dimensions). These are frequently based on assumptions on the precision of the axis system (like precise rotational axis). Algorithms from robotics are mostly based either on a tactile access or measurement by means of laser. Both variations cannot be applied for CT components. Previous approaches for CT systems can be subdivided to different principles.
 Methods for calculating the position of source and detector relative to the object and irrespective of the axis system
 Methods for calculating the basis and tool coordinate systems of industrial robots
 Methods for calibrating industrial robots are usually based on free accessibility of the tool or a way of being able to observe the same by means of optical methods. However, this is not possible for X-ray tubes and detectors used in CT since here the focal spot of the X-ray tube and the imaging plane of the detector are considered as a tool and these are not accessible. Only methods for determining the position of the basis of the manipulators will be discussed below.

UltraCal is an optical calibration method for determining the basis of two robots, which is based on a laser having an integrated sensor and a retroreflector.

The laser and the retroreflector are fixed to one robot each and aligned manually such that the deviation of the laser reflection in two space dimensions is approximately zero. By manipulating the robot position, the relative position of the robots relative to each other can be determined. This has to be performed for at least three points in space.

Similar to UltraCal, a point in space defined by, for example, a sphere is scanned by the robots or these contact one anther using special holders. The quantities, important for reconstruction, like the position of the focal space and the imaging plane, cannot be determined in this way.

There are many methods for determining the so-called misalignment of source and detector. The position of source and detector relative to the object coordinate system are determined here using different approaches. Almost every method either solves only a very limited quantity of degrees of freedom or is highly limited, e.g. relative to the trajectory followed (only circle, only helix, . . . ). Other methods use a fixed predetermined arrangement of spheres in an object or else an enormously high precision when manufacturing the body. These methods are additionally not suitable for calibrating the actual manipulators of the components. Consequently, there is demand for an improved approach.

The object underlying the present invention is providing a method for calibrating an X-ray system, in particular a computer tomography system, comprising radiation sources which can be moved independently of one another, and a radiation detector, which is improved with regard to ergonomics and calibration quality.

SUMMARY

According to an embodiment, a method for an X-ray-based calibration and adjustment of axis systems by means of an X-ray system having a radiation source and a radiation detector may have the steps of: establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations; setting the starting values for the parameters to be calibrated; and calibrating having the sub-steps of: establishing an X-ray projection of a calibration body for the first position on the movement trajectory in order to obtain a first measuring result for at least one feature of the calibration body; and comparing the first measuring result to a respective reference in order to determine an error measure; and solving the system of equations in order to determine the parameters to be calibrated; wherein the X-ray system has at least one robot or multi-element robot; wherein the robot or multi-element robot moves the radiation source, an object or the detector such that the radiation source, the object and/or the radiation detector are movable in dependence on machine parameters for driving the robot; and wherein the kinematic parameters of the set of kinematic parameters describe the kinematic model of the entire system having at least the robot or multi-element robot, wherein the kinematic parameters have non-variable kinematic parameters having a leg length of a component of the robot or multi-element robot, and variable kinematic parameters having the machine parameters which describe the movement or position of the respective joint of the robot or multi-element robot.

Another embodiment may have a non-transitory digital storage medium having stored thereon a computer program for performing a method for an X-ray-based calibration and adjustment of axis systems by means of an X-ray system having a radiation source and a radiation detector, having the steps of: establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations; setting the starting values for the parameters to be calibrated; and calibrating having the sub-steps of: establishing an X-ray projection of a calibration body for the first position on the movement trajectory in order to obtain a first measuring result for at least one feature of the calibration body; and comparing the first measuring result to a respective reference in order to determine an error measure; and solving the system of equations in order to determine the parameters to be calibrated; wherein the X-ray system has at least one robot or multi-element robot; wherein the robot or multi-element robot moves the radiation source, an object or the detector such that the radiation source, the object and/or the radiation detector are movable in dependence on machine parameters for driving the robot; and wherein the kinematic parameters of the set of kinematic parameters describe the kinematic model of the entire system having at least the robot or multi-element robot, wherein the kinematic parameters have non-variable kinematic parameters having a leg length of a component of the robot or multi-element robot, and variable kinematic parameters having the machine parameters which describe the movement or position of the respective joint of the robot or multi-element robot, when said computer program is run by a computer.

According to another embodiment, an apparatus for an X-ray-based calibration and adjustment of axis systems by means of an X-ray system having a radiation source and a radiation detector may have: a calculation unit for establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations, a calibrator configured, based on fixed starting values for the parameters to be calibrated, to: establish an X-ray projection of a calibration body for the first position on the movement trajectory in order to obtain a first measuring result for at least one feature of the calibration body; and comparing the first measuring result to a respective reference in order to determine an error measure; wherein the calibrator is configured to solve the system of equations in order to obtain the parameters to be calibrated; wherein the X-ray system has at least one robot or multi-element robot; wherein the robot or multi-element robot moves the radiation source, an object or the detector such that the radiation source, the object and/or the radiation detector are movable in dependence on machine parameters for driving the robot; and wherein the kinematic parameters of the set of kinematic parameters describe the kinematic model of the entire system having at least the robot or multi-element robot, wherein the kinematic parameters have non-variable kinematic parameters having a leg length of a component of the robot or multi-element robot, and variable kinematic parameters having the machine parameters which describe the movement or position of the respective joint of the robot or multi-element robot.

Another embodiment may have an X-ray system having a radiation source and an X-ray source, and an above inventive apparatus.

According to another embodiment, a method for an X-ray-based calibration and adjustment of axis systems by means of an X-ray system having a radiation source and a radiation detector, wherein the X-ray system has two multi-element robots; wherein a first one of the two robots moves the radiation source and the second one of the two robots moves the radiation detector so that the radiation source and/or the radiation detector is/are movable in dependence on machine parameters for driving the robots, may have the steps of: establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations; setting the starting values for the parameters to be calibrated; and calibrating having the sub-steps of: establishing an X-ray projection of a calibration body for the first position on the movement trajectory in order to obtain a first measuring result for at least one feature of the calibration body; and comparing the first measuring result to a respective reference in order to determine an error measure; and solving the system of equations in order to determine the parameters to be calibrated; wherein the parameters to be calibrated describe an offset of the radiation source relative to the robot, described in the kinematic model, which moves the radiation source; and/or wherein the parameters to be calibrated describe an offset between the X-ray detector and the kinematic model of the robot which moves the radiation detector.

According to another embodiment, an apparatus for an X-ray-based calibration and adjustment of axis systems by means of an X-ray system having a radiation source and a radiation detector, wherein the X-ray system has two multi-element robots; wherein a first one of the two robots moves the radiation source and the second one of the two robots moves the radiation detector so that the radiation source and/or the radiation detector is/are movable in dependence on machine parameters for driving the robots, may have: a calculating unit for establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations; a calibrator configured, based on fixed starting values for the parameters to be calibrated, to: establish an X-ray projection of a calibration body for the first position on the movement trajectory in order to obtain a first measuring result for at least one feature of the calibration body; and compare the first measuring result to a respective reference in order to determine an error measure; wherein the calibrator is configured to solve the system of equations in order to obtain the parameters to be calibrated; wherein the parameters to be calibrated describe an offset of the radiation source relative to the robot, described in the kinematic model, which moves the radiation source; and/or wherein the parameters to be calibrated describe an offset between the X-ray detector and the kinematic model of the robot which moves the radiation detector.

Another embodiment may have a non-transitory digital storage medium having stored thereon a computer program for performing a method for an X-ray-based calibration and adjustment of axis systems by means of an X-ray system having a radiation source and a radiation detector, wherein the X-ray system has two multi-element robots; wherein a first one of the two robots moves the radiation source and the second one of the two robots moves the radiation detector so that the radiation source and/or the radiation detector is/are movable in dependence on machine parameters for driving the robots, having the steps of: establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations; setting the starting values for the parameters to be calibrated; and calibrating having the sub-steps of: establishing an X-ray projection of a calibration body for the first position on the movement trajectory in order to obtain a first measuring result for at least one feature of the calibration body; and comparing the first measuring result to a respective reference in order to determine an error measure; and solving the system of equations in order to determine the parameters to be calibrated; wherein the parameters to be calibrated describe an offset of the radiation source relative to the robot, described in the kinematic model, which moves the radiation source; and/or wherein the parameters to be calibrated describe an offset between the X-ray detector and the kinematic model of the robot which moves the radiation detector, when said computer program is run by a computer.

Embodiments of the present invention provide a method for calibrating comprising the steps of determining a kinematic model of the X-ray system with all the kinematic relations for at least a first position on the movement trajectory, and describing the same using a first set of kinematic parameters and using parameters to be calibrated. The first set of kinematic parameters here, together with the parameters to be calibrated, defines a first equation of a system of equations. In the kinematic model, both the two robots having the radiation detector, or the radiation source, and, for example, a calibration body may be included in the kinematic model. The kinematic model is described by kinematic parameters. These may generally be formulated using means of linear algebra, like coordinate transformations, but also in more complex forms, like with (partial) differential equations. Alternatively, these may also be described using minimum representations, like Denavit-Hartenberg or Hayati-Roberts.

In a step after determining the kinematic models, the starting values for the parameters to be calibrated are set and a calibration process is started. The calibration process comprises determining an X-ray projection of the calibration body mentioned above for the first position on the movement trajectory in order to obtain a first measuring result for at least one feature of the calibration body. An error measure can be determined by comparing the first measuring result to the respective reference. The system of equations mentioned above may, for example, be solved by a simple zero position calculation or may be solved by minimizing the error measure (like using the Levenberg-Marquard algorithm). Here, the parameters to be calculated are, for example, varied until the error measure has reached a minimum, whereas the non-variable kinematic parameters of the kinematic model, like lengths of a leg of a robot, or variable kinematic parameters, like the machine parameters defining a joint position for the respective degree of freedom, cannot be varied.

The central idea of the present invention is based on the fact that, for calibrating the system, a complete kinematic model of the axis system is set up exclusively on the basis of X-ray projections measured (like Denavit-Hartenberg).

For determining the kinematic parameters to be solved, X-ray projections of a reference body are recorded in at least one, but advantageously in most different axis positions. The number of projections and axis positions here varies depending on the number of degrees of freedom to be solved. The error measure for the system of equations to be solved can be set in different ways and subsequently be minimized. On the one hand, the images or mappings or representations generated may serve as reference values for an error measure. With a reference body made of spheres, for example, the first or second-degree tensor of the sphere representation may be used as a reference. An alternative promising approach would be solving directly in the object instead of the projection space, like when the error measure compares the reconstructed spheres to the CAD model. A higher precision can be expected from this and additional aspects from the real system can be considered, like modeling the focal spot (currently pinhole camera model). The system of equations can be solved by means of a suitable search strategy (like non-linear optimization methods) based on the model. This means that the parameters searched are determined on the basis of the model and suitable starting values such that the representations generated using the model or reconstructions correspond to the reference data.

It is of advantage with the approach presented that a complete kinematic model of the axis system is or can be set up for calibrating the system exclusively based on the X-ray projections measured (like Denavit-Hartenberg). For determining the kinematic parameters to be solved, X-ray projections of a reference body are recorded in most different axis positions. The number of projections and axis positions here varies depending on the number of degrees of freedom to be solved. The error measure for the system of equations to be solved can be set in different ways and subsequently be minimized. On the one hand, the representations generated may serve as reference values for an error measure.

In correspondence with further embodiments, the steps of "establishing a kinematic model" can be repeated for a second position and "describing the same using a second set of kinematic parameters", "establishing an X-ray projection of the calibration body" for a second position (in order to obtain a second measuring result) and "comparing the (second) measuring result to the respective reference" (in order to determine the error measure again) can be repeated. The second set of kinematic parameters, together with the parameters to be calibrated, forms a second equation of the system of equations so that this approach allows finding several unknown parameters (to be calibrated). Here, it is assumed that the parameters to be calibrated are constant across the sets of kinematic parameters.

The system of equations can be solved by a suitable search strategy (like non-linear optimizing methods) on the basis of the model. This means that the parameters searched are determined on the basis of the model and suitable starting values such that the representations generated using the model or reconstructions correspond to the reference data. The reference body here may be part of the model so that its geometry can also be determined, if applicable.

This approach allows calibrating any axis system/manipulation system on the basis of X-ray projections of a reference body. In this context, calibrating particularly describes determining the coordinate transforms underlying the axis system and its configuration, with the goal of setting up a complete kinematic model of the axis system based on X-ray projections measured.

Even though the concept may be applied to any axis systems (like helix or rotation CTs), when assuming CT systems having one or several, like two (multi-element) robots which move the radiation source on the one hand and the radiation detector on the other hand, for example, the parameters to be calibrated may, for example, be the offset between the two robots which is to be determined more precisely. Further parameter to be calibrated may be the offset between radiation source and the known kinematic model of the robot or the offset between the X-ray detector and the kinematic model of the robot.

In a first approximation, these kinematic parameters are measured, for example, or read from a known data set, like CAD data. However, usually this result established by means of metrology is not sufficient in order to allow CT reconstructions.

In correspondence with an embodiment, the system of equations may, for example, be solved as follows:

$$\min_{\vec{u},\vec{p}} \left\| \frac{1}{NK} \sum_{n=1}^{N} \sum_{k=1}^{K} e_{n,k} \right\|_2,$$

wherein:

$$e_{n,k}(\vec{u},\vec{q}_n,\vec{p}_k) = \|f - f_{ref}\|_2; \text{ and}$$

wherein u describes the parameters to be calibrated and $f(\vec{u}, \vec{q}, \vec{p}) \rightarrow \vec{p}_e$ when only one feature of the calibration object is used, or $f(\vec{u},\vec{q}_n,\vec{p}_k) \rightarrow \vec{p}_k'$ when several features of the calibration body are established by several projections. q here describes the respective machine coordinates, i.e. the joint positions of the axis system, described using the coordinates of the kinematic model, and wherein p and $p_k$ describe the position of the feature and features of the calibration body, respectively, for the first and/or the second measuring result with the coordinate system of the kinematic model. P' and $p_k'$ describe the position of the representation of the feature/the features on the detector with the coordinates of the kinematic model.

In correspondence with embodiments, the respective references are formed by the first or second-degree tensor. This variation is particularly suitable for calibration objects made of spheres. In correspondence with further embodiments, the following formula may be employed here:

$$M_{pq} = \int_{-\infty}^{\infty} \int_{-\infty}^{\infty} x^p y^q f(x, y) dx dy$$

Alternatively, the respective reference may also be established by means of computing, like when knowing the position of the calibration body and the geometry of the calibration body.

It is to be pointed out here that, in correspondence with embodiments, the position model of the respective radiation source-detector pair is also taken into consideration. This is done using the following formula, for example:

$$\begin{bmatrix} v_x & w_x & d_x - s_x \\ v_y & w_y & d_y - s_y \\ v_z & w_z & d_z - s_z \end{bmatrix} \begin{bmatrix} \lambda x' \\ \lambda y' \\ \lambda \end{bmatrix} = \begin{bmatrix} p_x - s_x \\ p_y - s_y \\ p_z - s_z \end{bmatrix},$$

wherein $p_x$, $p_y$ and $p_z$ describe the position of the feature of the calibration body in space, wherein $s_x$, $s_y$, and $s_z$ describe the position of the projection center in space, wherein $d_x$, $d_y$, and $d_z$ describe the position of the imaging plane in space, and wherein $v_x$, $v_y$ and $v_z$ and $\omega_x$, $\omega_y$ and $\omega_z$ refer to the planar basis vectors. S, d, v and ω are described by the coordinates of the kinematic model.

A further embodiment relates to a corresponding apparatus executing the method described above. A calculating unit for establishing the kinematic models and a calibrator for performing the calibration method are provided here.

A further embodiment relates to a computer program for performing any of the methods described here. This may allow automation of the method, i.e. with no user interaction.

A further embodiment relates to an X-ray system comprising, for example, two robots able to move the radiation source and the X-ray source, and the apparatus as described before or a computer for performing any of the methods described herein. In correspondence with further embodiments, the apparatus mentioned above and/or the computer may also comprise an interface for controlling the X-ray system or a controller for controlling the robot of the X-ray system.

BRIEF DESCRIPTION OF THE DRAWINGS

Embodiments of the present invention will be discussed referring to the appended drawings, in which:

FIGS. 2a, b show tables for illustrating kinematic parameters or kinematic variables.

DETAILED DESCRIPTION OF THE INVENTION

Figure 1A:
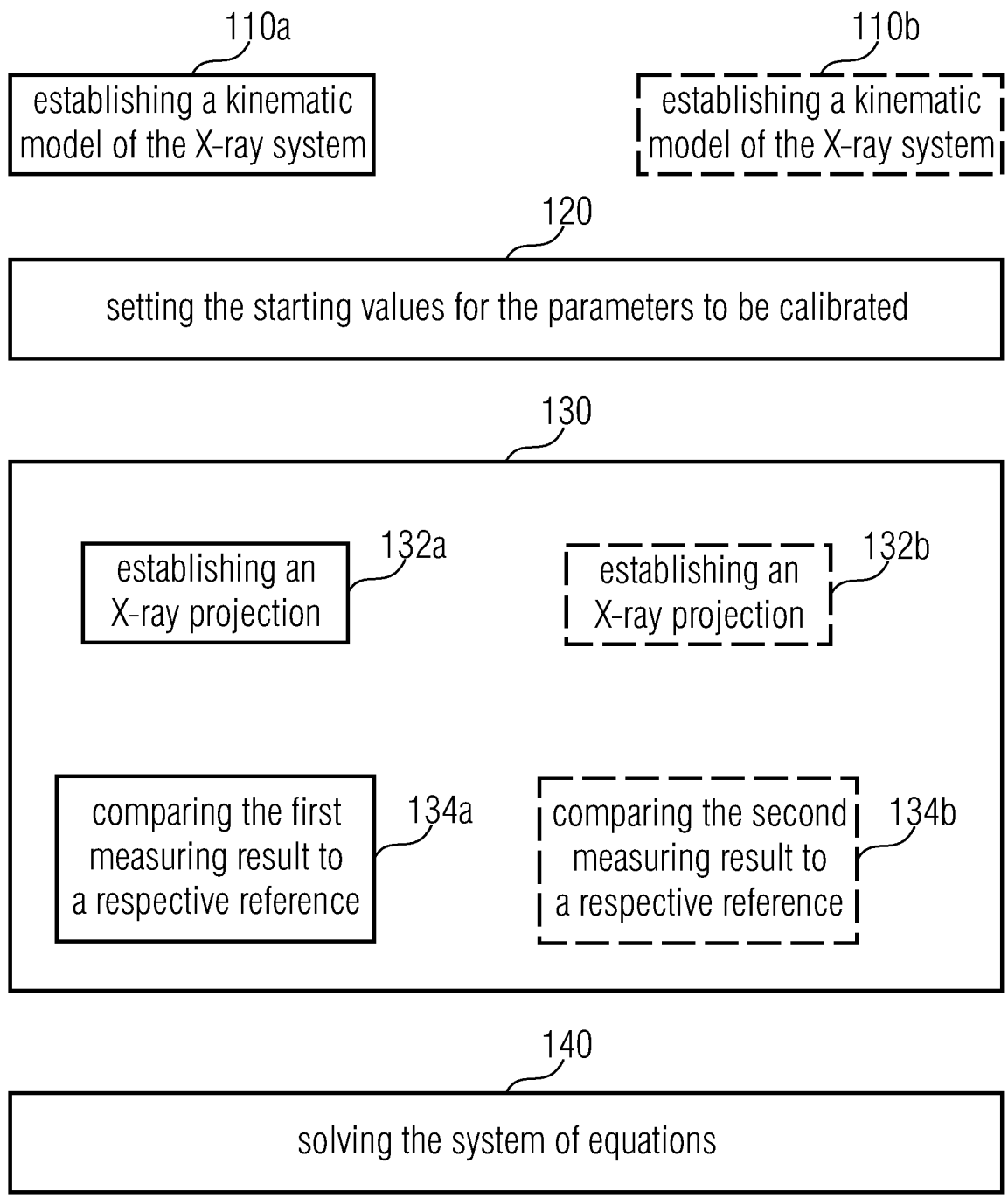
FIG. 1a shows a schematic flowchart of the method for calibrating an X-ray system comprising a movable radiation source and a movable radiation detector in accordance with an embodiment.

Before describing below in greater detail embodiments of the present invention referring to the appended drawings, it is to be pointed out that elements and structures of equal effect are provided with equal reference numerals so that the description thereof is mutually applicable and/or interchangeable.

FIG. 1a show the basic steps of a method 100 for calibrating. The method 100 comprises basic step 110a, optional step 110b and basic steps 120, 130 and 140, step 130 comprising a plurality of sub-steps.

Figure 1B:
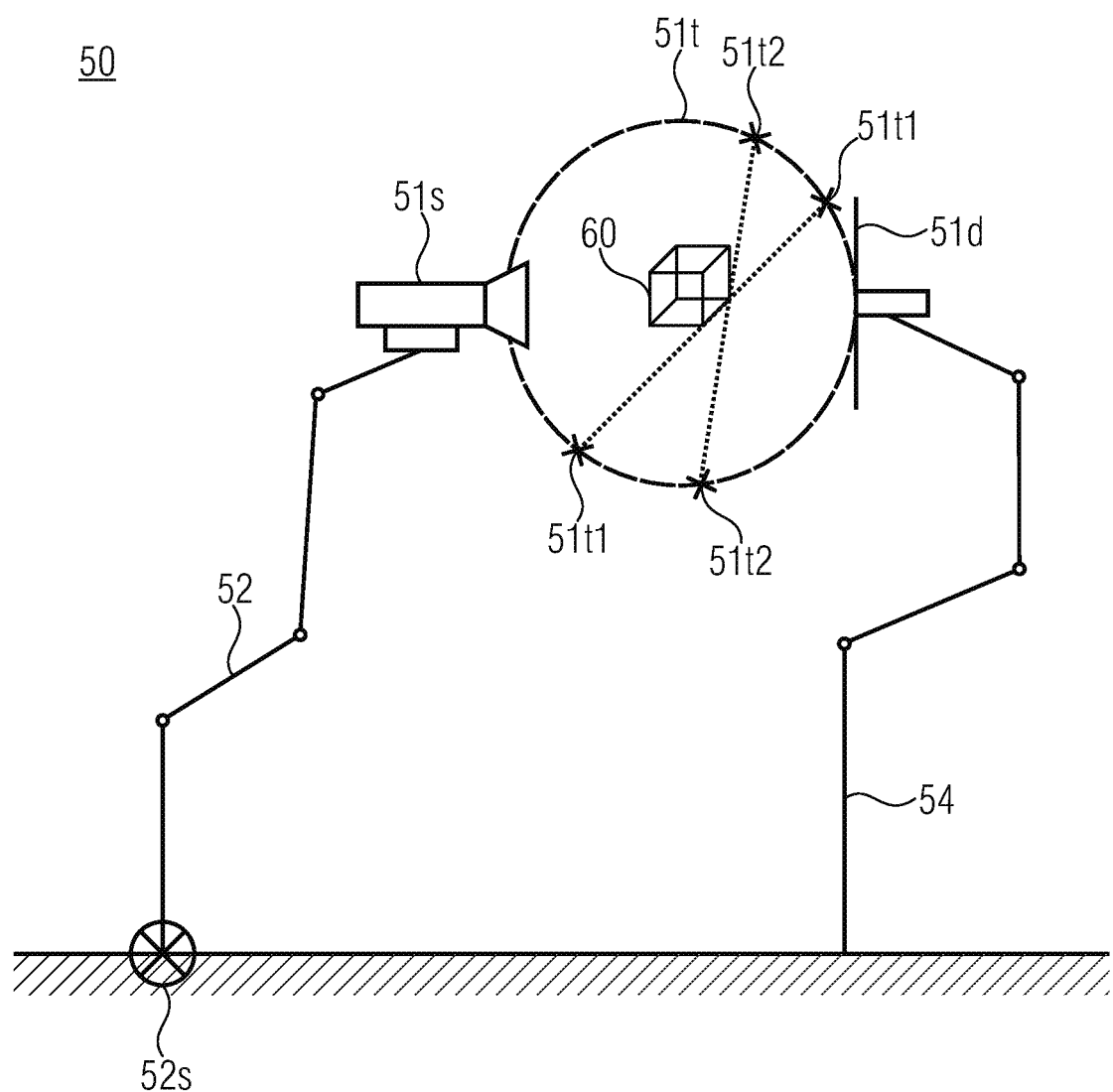
FIG. 1b shows a schematic block circuit diagram of two multi-element robots for moving the radiation source and radiation detector in accordance with an embodiment.

Steps 110a and 110b are basically equal, wherein mandatory step 110a is performed for a first position on a movement trajectory of the X-ray system (cf. system 50 in FIG. 1b) and optional step 110b for a second position of the X-ray system. Reference here is made to FIG. 1b.

FIG. 1b shows two robots 52 and 54, in this case multi-element robots, robot 52 holding the radiation source 51s and robot 54 holding the X-ray detector 51d. The radiation source 51s and the detector 51d are, for example, movable along the dotted movement trajectory 51t (trajectory) of the X-ray system 50. There are a number of positions on this trajectory, wherein step 110a is performed for a position 51t1 (cf. crosses) and step 110b is performed for a position 51t2. As can be recognized, there are two crosses 51t1 and 51t2 each, since two respective positions for radiation detector 51d and radiation source 51s belong to a position on the trajectory. The two positions need not necessarily be located within one plane, but may be arranged at any other angle in space around the object 60 or test object.

Steps 110a and 110b of establishing a kinematic model of the X-ray system 50 with all the kinematic relations for the first and second position 51t1 and 51t2 on the movement trajectory 51t are performed at these two positions 51t2 and 51t1. In step 110a and 110b, kinematic parameters of a set of kinematic parameters are established, describing the kinematic model of the entire system comprising the robots 52 and 54 for moving the radiation source 51s and the radiation detector 51d.

The first set of kinematic parameters established in step 110a and the second set of kinematic parameters established in step 110b may, for example, be detected by means of the nomenclature pursuant to Denavit-Hartenberg. The Denavit-Hartenberg convention allows transferring position coordinate systems within kinematic chains. Thus, it is possible to describe a robot, in particular a multi-element robot, as is shown in FIG. 1b, using Denavit-Hartenberg parameters or using homogenous matrices such that it becomes clear how the same is set up (two-element, three-element, . . . ) and dimensioned (short legs, long legs) and also what its position is relative to a fixed point. According to the Denavit-Hartenberg convention, the following conditions are needed:
1. The $z_{n-1}$ axis is located along the movement axis of the n-th joint.
2. The $x_n$ axis is the cross product of the $z_{n-1}$ axis and the $z_n$ axis.
3. The coordinate system is supplemented by yn such that the result is a right-handed system. The consequence is that, for the first joint, the x axis is taken over by the second joint.

In correspondence with the Denavit-Hartenberg convention, there are different parameters including (1) non-variable kinematic parameters, like leg lengths of the robots 52 and 54, (2) variable kinematic parameters, like the machine parameters, the movement or position of the respective joint of the multi-element robots 52 and 54, and (3) the parameters to be calibrated. The parameters to be calibrated are those values relative to which the value is not known or not known exactly. These may, for example, relate to the relative position of the two robots 52 and 54 relative to each other or the length of a leg where there is uncertainty about the correctness of the assumed values.

It is to be pointed out here that both robots 52 and 54 may be described in a common kinematic model in correspondence with the Denavit-Hartenberg convention, wherein robot 54, for example, is described in the model of robot 52, i.e. around the origin or position around the robot 52 (cf. point 52s). When compared to robot 52, robot 54 exhibits an offset, i.e. the distance between these two robots, which usually is a parameter to be calibrated, since positioning may vary here. Consequently, this parameter to be calibrated, i.e. the distance between the two robots 52 and 54, usually also has to be calibrated using method 100.

Since both the first set of kinematic parameters from step 110a and the second set of kinematic parameters from step 110b relate to the same X-ray system 50 and, thus, also to the same robot arrangement of robots 52 and 54, these two data sets differ only with regard to the machine parameters since position 51t2 was obtained from position 51t1 by changing the machine parameters. Expressed differently, this means that the non-variable kinematic parameters, like the axis length, and the parameters to be calibrated, like the distance between robots 52 and 54, are constant in both kinematic parameter data sets.

This characteristic is made use of in step 130 of calibrating, wherein, before calibrating, starting values for the parameters to be calibrated have to be set in order to perform the calibration process. These parameters to be calibrated are provided with values in step 120. Here, the values may, for example, originate from measurements, like made by means of laser measuring apparatuses, or from construction data for the X-ray system 50.

The step of calibrating 130 comprises at least two and, in the variation presented here, four sub-steps 132a/132b and 134a/134b, wherein sub-steps 134a/134b for the second position (like before) are optional.

Step 132, both a and b, relates to establishing an X-ray projection of a calibration body 60 (cf. FIG. 1b), wherein step a is performed for the position 51t1 and step b for position 51t2. The result of steps 132a and b are measurements, like a representation of a center of gravity (as a feature) of the calibration body 60 on the X-ray detector 51d, and more precisely, on a position of the X-ray detector 51d. It is to be pointed out here that the position of the calibration body 60 or, in particular, the position of the feature of the calibration body 60 using which calibration is done (or of the features using which calibration is done), are also included in the kinematic model, which means that the kinematic model is described using the coordinate system.

The calibration body 60 or reference body may, for example, be such so as to contain sufficient information in relation to the structures or features obtained. These features may, for example, originate from a CAD model. Such an object may exemplarily consist of any arrangement of spheres. No specific requirements relating to precision or arrangement of the spheres are made to the reference body 60. Thus, the reference body may be part of the model so that its geometry can also be determined, if applicable. Generally, even the object to be measured can be used as reference body.

In a reference body 60 made of spheres, for example, the first or second-degree tensor of the sphere representation may be used as a reference. An alternative, promising approach would be solving this directly in the object, instead of the projection space, for example, by the error measure comparing the reconstructed spheres to the CAD model. An increased precision could be expected from this and additional aspects from the real system could be considered, like modeling the focal spot (currently pinhole camera model).

Based on the then known projection position, when calibrating, these can be compared to an expected reference, i.e., for example, to a projection position established by means of calculating or to a projection reference derived from the measurement itself, in order to determine a so-called error measure. This step is performed for both measuring step 132a and measuring step 132b in steps 134a and 134b.

When, in a subsequent step, this error measure is minimized by correspondingly adjusting the parameters to be calibrated, for example, the result will be the calibration data searched. This step corresponds to central step 140 since minimizing here is performed by solving a system of equations. In the system of equations, there is one kinematic equation contained per position 51t1 and 51t2, i.e. this is a system of equations having several equations and several variables so that these are solvable by adding any number of new equations by new calibration processes for further positions. Alternatively, the system of equations can also be solved by means of simply determining the zero position.

Figure 1C:
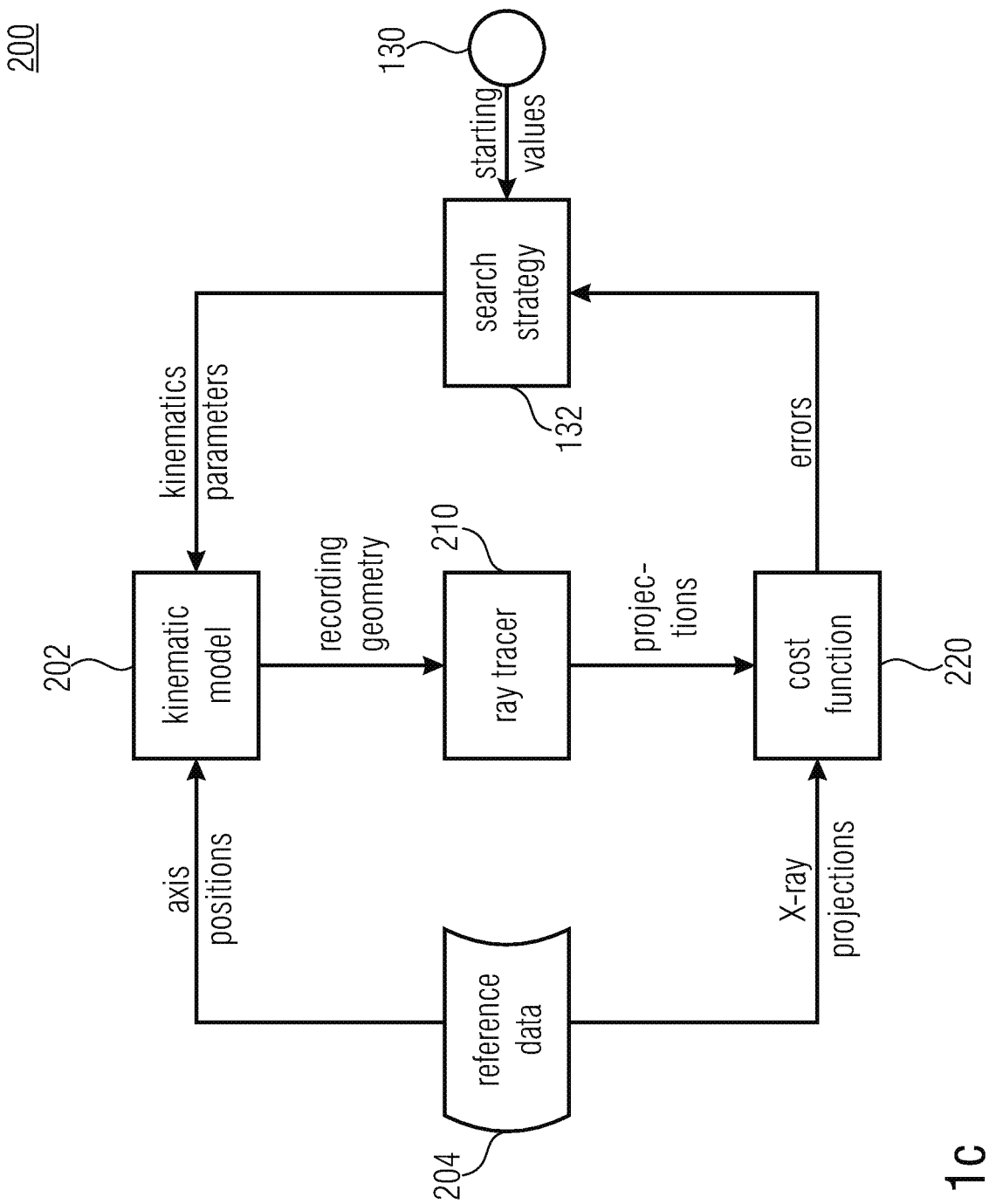
FIG. 1c shows a schematic flowchart of an extended method when calibrating an X-ray system comprising a movable radiation source and a movable radiation detector in accordance with a further embodiment.

As is illustrated in FIG. 1c, the method may also be embodied to be somewhat more complex. FIG. 1c shows the method 200 comprising the steps of setting 130 starting values, defining 132 a search strategy 132 based on the kinematic parameters set in the kinematic model 202.

Apart from kinematic parameters, the kinematic model 202 also comprises the axis positions, i.e. the machine commands originating from the reference data 204. Based on the now set kinematic model 202, the recording geometries are derived and the corresponding projections (cf. ray tracer 210 step) are taken. The horizon of expectation for the X-ray projections which are then compared by means of a cost function (cf. step 220) are also derived from the reference data. The error is derived from this and, in correspondence with embodiments, the search strategy (cf. step 132) is adjusted correspondingly.

The method present here cannot only be applied to any axis systems and in an automated manner, but it is additionally not necessary to make assumptions relating to the recording geometry (i.e., above all, in relation to the trajectories used, like circle, helix) and relating to the beam geometry, like cone, fan or parallel beam. Additionally, no high-precision reference body is necessary since the same may also be calibrated, if applicable in the method.

The mathematical model will be discussed making use of a specific example referring to FIG. 2. The method is illustrated using a system consisting of two RX90B robots manufactured by Stäubli Company, and a flat image detector and an X-ray tube having a cone beam.

In a first step, as is discussed referring to FIG. 1a, the kinematic model is set up. An example of such a kinematic model is illustrated in FIG. 2a. FIG. 2a shows the Denavit-Hartenberg parameters of the RX90B robot. Making reference to the picture in FIG. 1b, exemplarily the first robot 52 supporting the radiation source 51s will be described. The distances are indicated in millimeters, the angles in dependence on p. It is to be mentioned here that 0 represents the respective machine coordinates for the respective joints 1 to 6. The respective chain describes the beginning and the end of a manipulator.

The first step includes setting up the kinematic model of the manipulation system. Here, the Denavit-Hartenberg parameters for the RX90B robot are established and extended such that the entire system is understood to be kinematics. The origin of the world coordinate system here, for reasons of simplicity, is to equal the origin of the robot coordinate system for the robot having the X-ray tube.

As has already been discussed above, the posture of the second robot is included in the same kinematic model or system of equations, so that the Hartenberg parameters from FIG. 2a are extended by the second robot and the result will be the Hartenberg parameters from FIG. 2b. The Hartenberg parameters from FIG. 2b describe the entire kinemb3). Furthermore, this parameter data set has also been extended by the offset which the radiation source 51s exhibits, for example due to its suspension, and the radiation detector 51d exhibits, for example due to its suspension. Here, the parameter dataset is extended by the parameters searched or parameters to be optimized/calibrated for the detector in lines d0 to d3 and for the sensor in line s0 to s3.

Based on this kinematic model, a system of equations with the unknown quantities d0 to d3 or b0 to b3 or s0 to s3 can be set up, which can then be solved, as discussed before referring to FIG. 1a.

Here, as has already been explained, the starting values for the parameters to be calibrated are inserted. Starting values for [s0, s1 s2, s3] and [d0, d1, d2, d3] are taken from the CAD data of the holder. The starting values for [b0, b1, b2, b3] are determined using laser distance measuring devices.

In this embodiment, the projection model is also used during calibration.

From a mathematical point of view, taking an image using an area detector corresponds to a central projection. All the beams are emitted by a point source. The formation of the representation is defined by the position of the projection center $\vec{s}$ and the projection plane, described by a plane tracing point $\vec{d}$ and the plane basis vectors $\vec{v}$ and $\vec{w}$.

The quantities $\vec{s}$, $\vec{d}$, $\vec{v}$ and $\vec{w}$ needed for calculating a projection can be calculated on the basis of machine coordinates ($\theta$) and the forward kinematics from the kinematic model.

$$\begin{bmatrix} v_x & w_x & d_x - s_x \\ v_y & w_y & d_y - s_y \\ v_z & w_z & d_z - s_z \end{bmatrix} \begin{bmatrix} \lambda x' \\ \lambda y' \\ \lambda \end{bmatrix} = \begin{bmatrix} p_x - s_x \\ p_y - s_y \\ p_z - s_z \end{bmatrix}$$

The mathematical model will be discussed using a specific example making reference to FIG. 2.

Different variations of determining the reference for the calibration and the reference body will be discussed below.

The second-degree tensor (center of gravity) from a sphere representation is used as a reference. X-ray projections of a calibration body consisting of eight spheres are taken here. Using the image processing chain shown, the reference data needed are generated. Segmenting the sphere representation and determining the tensors up to the n-th degree (n=2, for example).

$$M_{pq} = \int_{-\infty}^{\infty} \int_{-\infty}^{\infty} x^p y^q f(x, y) dx dy$$

As has already been explained, it would, however, also be conceivable to use a CAD model as an alternative to the tensors, from which a higher precision can be expected in order to consider additional aspects from the real system, like modeling the focal spot, for example.

After determining the reference values, an error measure, i.e. the deviation between the actually projected position and the expected projected position, can be established.

On the basis of the reference values, the respective stored machine coordinates q and the kinematic model, the following error measure can be defined in dependence on the unknown parameters u=[s0, s1, s2, s3, d0, d1, d2, d3, b0, b1, b2, b3]:

$$f(\vec{u}, \vec{q}, \vec{p}) \rightarrow \vec{p}_e$$

Wherein $\vec{p}$ represents any object point and $\vec{p}_e$ represents its representation on the detector. If the calibration body comprises several spheres k and n projections are taken, the following applies:

$$f(\vec{u}, \vec{q}_n, \vec{p}_k) \rightarrow \vec{p}_k'$$

Every reference point can be interpreted as a solution of this function. In this case, the error measure will be as follows:

$$e_{n,k}(\vec{u}, \vec{q}_n, \vec{p}_k) = \|f - f_{ref}\|_2$$

A solution $\vec{u}$ can be found by solving the following system of equations:

$$\min_{\vec{u},\vec{p}} \left\| \frac{1}{NK} \sum_{n=1}^{N} \sum_{k=1}^{K} e_{n,k} \right\|_2$$

As has been discussed before, this error measure of the different measuring value is minimized, which basically represents an optimization task. Exemplarily, the error measure can be minimized using the Levenberg-Marquard algorithm in order to determine a solution for the degrees of freedom searched or the parameters to be calibrated. As an alternative to solving the system of equations by applying the optimization algorithm in accordance with Levenberg-Marquard (optimization algorithms for a numerical solution of the decrease in gradients), an analytical solution can be sought or further optimization algorithms can be applied for a numerical solution, like decrease in gradients or heuristic algorithms, like Downhill-Simplex.

Even when, in the above embodiment, at least two positions moved to were assumed so that two equations are defined by the two positions, it is to be pointed out here that, in principle, one position is sufficient, for example when there is only a single parameter to be calibrated, or several equations can be obtained from the projection recording from the first position, for example based on several features of the calibration body.

In the above embodiments, additionally, axis systems may be adjusted at lower precision. Dynamic influences during recording may also be detectable (for example, due to gravitation by different positions of a robot or due to a migrating focal spot).

In correspondence with one embodiment, instead of or apart from the position of the calibration body, the calibration body itself or a geometry thereof can be determined as the parameter to be calibrated, and consequently be calibrated.

The method is needed particularly for robot-assisted computer tomography systems since here usually two or more industrial robots are positioned freely in space and the X-ray components are mounted manually thereto. In order to perform a CT, the relative position of the robots among one another and the position of the focal spot and the imaging plane have to be known. This also allows calibrating systems where robots are used for manipulating the object to be measured (FlexCT, DragonFly, etc.).

It is to be pointed out again here that the trajectory of a CT system may originate from any relative movement between radiation source/radiation detector and object. This means that the method described above is applicable to any CT system (rotation, helix, freely movable radiation source and/or radiation detector, moved object in combination with fixed radiation source/radiation detector, . . . ).

Furthermore, the method may be employed for adjusting laboratory systems since similar problems apply here relative to the manipulators used. In particular, the position of the axes in reality does not correspond exactly to the specified values. When replacing X-ray components, such systems usually have to be re-adjusted manually, which is complicated. Calibration using the method presented either allows easier adjusting or reconstructing using the error quantities known. This can allow very large savings in time for the user.

In axis systems of very low precision, the geometry parameters used for reconstruction can be calculated from specific positions of the axis system for a specific measurement, thus allowing high-quality reconstruction.

Dynamic influences, like deformation of the axis system due to gravity, with high a weight of the X-ray components, can be detected, and, if applicable, compensated. Effects, like a migrating focal spot during measurement, may be part of the model and be observed using it.

Even when the above embodiments were discussed in relation to one or several robots, in particular multi-element robots, it is to be pointed out that robots here also include simple linear drives and other manipulators.

Although some aspects have been described in the context of an apparatus, it is clear that these aspects also represent a description of the corresponding method, such that a block or device of an apparatus also corresponds to a respective method step or a feature of a method step. Analogously, aspects described in the context of or as a method step also represent a description of a corresponding block or item or feature of a corresponding apparatus. Some or all of the method steps may be executed by (or using) a hardware apparatus, like, for example, a microprocessor, a programmable computer or an electronic circuit. In some embodiments, some or several of the most important method steps may be executed by such an apparatus.

Depending on certain implementation requirements, embodiments of the invention can be implemented in hardware or in software. The implementation can be performed using a digital storage medium, for example a floppy disk, a DVD, a Blu-Ray disc, a CD, an ROM, a PROM, an EPROM, an EEPROM or a FLASH memory, a hard drive or another magnetic or optical memory having electronically readable control signals stored thereon, which cooperate or are capable of cooperating with a programmable computer system such that the respective method is performed. Therefore, the digital storage medium may be computer-readable.

Some embodiments according to the invention include a data carrier comprising electronically readable control signals, which are capable of cooperating with a programmable computer system such that one of the methods described herein is performed.

Generally, embodiments of the present invention can be implemented as a computer program product with a program code, the program code being operative for performing one of the methods when the computer program product runs on a computer.

The program code may, for example, be stored on a machine-readable carrier.

Other embodiments comprise the computer program for performing one of the methods described herein, wherein the computer program is stored on a machine-readable carrier.

In other words, an embodiment of the inventive method is, therefore, a computer program comprising a program code for performing one of the methods described herein, when the computer program runs on a computer.

A further embodiment of the inventive methods is, therefore, a data carrier (or a digital storage medium or a computer-readable medium) comprising, recorded thereon, the computer program for performing one of the methods described herein.

A further embodiment of the inventive method is, therefore, a data stream or a sequence of signals representing the computer program for performing one of the methods described herein. The data stream or the sequence of signals may, for example, be configured to be transferred via a data communication connection, for example via the Internet.

A further embodiment comprises processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer a computer program for performing at least one of the methods described herein to a receiver. The transmission can be performed electronically or optically. The receiver may, for example, be a computer, a mobile device, a memory device or a similar apparatus. The apparatus or system may, for example, comprise a file server for transferring the computer program to the receiver.

In some embodiments, a programmable logic device (for example a field-programmable gate array, FPGA) may be used to perform some or all of the functionalities of the methods described herein. In some embodiments, a field-programmable gate array may cooperate with a microprocessor in order to perform one of the methods described herein. Generally, in some embodiments, the methods are performed by any hardware apparatus. This can be a universally applicable hardware, such as a computer processor (CPU), or hardware specific for the method, such as ASIC.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

LITERATURE

UltraCal Laser-based Robot Calibration System. Robo-Technology GmbH. http://www.robotechnology.de/UltraCal_V5.pdf, online, as of Dec. 5, 2012.

Cheng, F. S. Calibration of robot reference frames for enhanced robot positioning accuracy. Technical report, Central Michigan University.

Heyer, T., Grigorescu, S. M., and Gräser, A. Camera calibration for reliable object manipulation in care-providing robot friend. Technical report, Institute of Automation (IAT), University of Bremen.

Hu, Z., Gui, J., Zou, J., Rong, J., Zhang, Q., Zheng, H., and Xia, D. Geometric Calibration of a Micro-CT System and Performance for Insect Imaging. http://ieeexplore.ieee.org/stamp/stamp.jsp?arnumber=5871720, retrieved on May 20, 2016.

Mery, D., Geisert, C., and Filbert, D. Geometric Calibration of a X-ray Testing System. Technische Universität Berlin. http://www.ndt.net/article/v07n03/mery02/mery02.htm, online, as of Dec. 12, 2012.

Stopp, F., Wieckowski, A. J., Käseberg, M., Engel, S., Fehlhaber, F., and Keeve, E. A Geometric Calibration Method for an Open Cone-Beam CT System. Charité Universitätsmedizin Berlin. https://www.researchgate.net/publication/236324982_A_Geometric_Calibration_Method_for_an_Open_Cone-Beam_CT_System, online, as of Dec. 12, 2012.

Sun, Y., Hou, Y., Zhao, F., and Hu, J. A Calibration Method for Misaligned Scanner Geometry in Cone-beam Computed Tomography. Technische Universität Berlin. http://www.ndt.net/article/v10 n09/yisun/yisun.pdf, online, as of Dec. 12, 2012.

Wang, W., Liu, F., and Yun, C. Calibration method of robot base frame using unit quaternion form. Technical report, Central Michigan University.

Yahui, G. and Xianzhong, D. (2011). Base frame calibration for coordinated industrial robots. Technical report, School of Automation, Southeast University, Nanjing, 210096, PR China.

Yang, K., Kwan, A. L. C., Miller, D. F., and Boonea, J. M. A geometric calibration method for cone beam CT systems. http://www.ncbi.nlm.nih.gov/pmc/articles/PMC2840998/, retrieved on May 20, 2016.

Zhao, J., Hu, X., Zou, J., and Hu, X. Geometric Parameters Estimation and Calibration in Cone-Beam Micro-CT. http://www.mdpi.com/1424-8220/15/9/22811/pdf, retrieved on May 2016.

The invention claimed is:

1. A method for an X-ray-based calibration and adjustment of axis systems by means of an X-ray system comprising a radiation source and a radiation detector, comprising:
    establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations;
    setting the starting values for the parameters to be calibrated; and
    calibrating comprising:
        establishing an X-ray projection of a calibration body for the first position on the movement trajectory in order to acquire a first measuring result for at least one feature of the calibration body; and
        comparing the first measuring result to a respective reference in order to determine an error measure; and
        solving the system of equations in order to determine the parameters to be calibrated;
    wherein the X-ray system comprises at least one robot or multi-element robot; wherein the robot or multi-element robot moves the radiation source, an object or the detector such that the radiation source, the object and/or the radiation detector are movable in dependence on machine parameters for driving the robot; and
    wherein the kinematic parameters of the set of kinematic parameters describe the kinematic model of the entire system comprising at least the robot or multi-element robot,
    wherein the kinematic parameters comprise non-variable kinematic parameters comprising a leg length of a component of the robot or multi-element robot, and variable kinematic parameters comprising the machine parameters which describe the movement or position of the respective joint of the robot or multi-element robot.

2. The method in accordance with claim 1, wherein parameters to be calibrated which are valid for at least two or all of the points on the movement trajectory are determined when solving the system of equations.

3. The method in accordance with claim 1, wherein establishing a kinematic model of the X-ray system with all the kinematic relations is repeated for a second position on the movement trajectory in order to describe all the kinematic relations for a second position with a second set of kinematic parameters and using the parameters to be calibrated, wherein the second set of kinematic parameters and the parameters to be calibrated define a second equation of the system of equations; and wherein calibrating comprises:
  establishing an X-ray projection of the calibration body for the second position on the movement trajectory in order to acquire a second measuring result for at least one feature of the calibration body; and
  comparing the second measuring result to a respective reference in order to re-determine an error measure.

4. The method in accordance with claim 1, wherein the first and the second set of kinematic parameters are equal relative to the non-variable kinematic parameters and differ relative to the machine parameters which define a joint position for the respective degree of freedom; and
  wherein the parameters to be calibrated are constant over the sets of kinematic parameters.

5. The method in accordance with claim 1, wherein each set of kinematic parameters is definable using minimum representations, minimum representations in accordance with Denavit-Hartenberg or in accordance with the Hayati-Roberts model.

6. The method in accordance with claim 1, wherein the X-ray system comprises two multi-element robots;
  wherein a first one of the two robots moves the radiation source and the second one of the two robots moves the radiation detector so that the radiation source and/or the radiation detector is/are movable in dependence on machine parameters for driving the robots.

7. The method in accordance with claim 6, wherein the parameters to be calibrated describe an offset of the two robots; and/or
  wherein the parameters to be calibrated describe an offset of the radiation source relative to the robot, described in the kinematic model, which moves the radiation source; and/or
  wherein the parameters to be calibrated describe an offset between the X-ray detector and the kinematic model of the robot which moves the radiation detector.

8. The method in accordance with claim 1, wherein the kinematic model comprises all the relations for moving the radiation source, for moving the radiation detector and for the position of the calibration object in space.

9. The method in accordance with claim 8, wherein the parameters describing the position of the calibration object in space comprise at least one parameter to be calibrated.

10. The method in accordance with claim 8, wherein the parameters describing the geometry of the calibration object comprise at least one parameter to be calibrated.

11. The method in accordance with claim 1, wherein the system of equations is defined by:

$$\min_{\vec{u},\vec{p}} \left\| \frac{1}{NK} \sum_{n=1}^{N} \sum_{k=1}^{K} e_{n,k} \right\|_2,$$

with the following error measure:

$$e_{n,k}(\vec{u},\vec{q}_n,\vec{p}_k) = \|f - f_{ref}\|_2,$$

wherein u describes the parameters to be calibrated and $f(\vec{u},\vec{q},\vec{p}) \to \vec{p}_e$ describes a mapping function when using only one feature of the calibration object, or u describes the parameters to be calibrated and $f(\vec{u},\vec{q}_n,\vec{p}_k) \to \vec{p}_k'$ describes a mapping function when several features of the calibration body are established by means of several projections, wherein q describes the respective reference with the coordinates of the kinematic model, and wherein p describes the feature of the calibration body for the first and/or the second measuring result with the coordinate system of the kinematic model, wherein $p_k$ describes the features of the calibration body for the first and/or second measuring result in the coordinates of the kinematic model, and wherein p' describes mapping the feature on the detector with the coordinates of the kinematic model, and $p_k'$ describes mapping of the respective feature on the detector with the coordinates of the kinematic model.

12. The method in accordance with claim 1, wherein solving the system of equations comprises analytically solving or applying an optimizing algorithm in accordance with Levenberg-Marquardt or a heuristic algorithm in accordance with Downhill-Simplex.

13. The method in accordance with claim 1, wherein setting the starting values comprises establishing, by means of measuring technology, a relation between the two robot origins, determining a geometry of the holder for the radiation source and/or determining a geometry of a holder for the radiation detector.

14. The method in accordance with claim 1, wherein the calibration body comprises a plurality of spheres, and wherein the respective reference is formed by the first-degree tensor and/or by the second-degree tensor.

15. The method in accordance with claim 14, wherein the respective reference is determined using the following formula:

$$M_{pq} = \int_{-\infty}^{\infty} \int_{-\infty}^{\infty} x^p y^q f(x,y) dx dy$$

16. The method in accordance with claim 1, wherein the calibration body is known and the respective reference is established by means of calculating.

17. The method in accordance with claim 1, wherein the projection model of the respective pair of radiation source and radiation detector is considered when calibrating.

18. The method in accordance with claim 17, wherein the projection model is defined by the following formula:

$$\begin{bmatrix} v_x & w_x & d_x - s_x \\ v_y & w_y & d_y - s_y \\ v_z & w_z & d_z - s_z \end{bmatrix} \begin{bmatrix} \lambda x' \\ \lambda y' \\ \lambda \end{bmatrix} = \begin{bmatrix} p_x - s_x \\ p_y - s_y \\ p_z - s_z \end{bmatrix},$$

wherein $p_x$, $p_y$, and $p_z$ describe the position of the feature of the calibration body in space, wherein $s_x$, $s_y$, and $s_z$ describe the position of the projection center in space, wherein $d_x$, $d_y$ and $d_z$ describe the position of the reference in space, wherein $v_x$, $v_y$ and $v_z$ and $\omega_x$, $\omega_y$ and $\omega_z$ are the planar basis vectors, wherein s, d, v and ω are described by the coordinates of the kinematic model.

19. A non-transitory digital storage medium having stored thereon a computer program for performing a method for an X-ray-based calibration and adjustment of axis systems by means of an X-ray system comprising a radiation source and a radiation detector, comprising:
   establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations;
   setting the starting values for the parameters to be calibrated; and
   calibrating comprising:
      establishing an X-ray projection of a calibration body for the first position on the movement trajectory in order to acquire a first measuring result for at least one feature of the calibration body; and
      comparing the first measuring result to a respective reference in order to determine an error measure; and
      solving the system of equations in order to determine the parameters to be calibrated;
   wherein the X-ray system comprises at least one robot or multi-element robot; wherein the robot or multi-element robot moves the radiation source, an object or the detector such that the radiation source, the object and/or the radiation detector are movable in dependence on machine parameters for driving the robot; and
   wherein the kinematic parameters of the set of kinematic parameters describe the kinematic model of the entire system comprising at least the robot or multi-element robot, wherein the kinematic parameters comprise non-variable kinematic parameters comprising a leg length of a component of the robot or multi-element robot, and variable kinematic parameters comprising the machine parameters which describe the movement or position of the respective joint of the robot or multi-element robot,
   when said computer program is run by a computer.

20. An apparatus for an X-ray-based calibration and adjustment of axis systems by means of an X-ray system comprising a radiation source and a radiation detector, comprising:
   a calculation unit for establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations,
   a calibrator configured, based on fixed starting values for the parameters to be calibrated, to:
      establish an X-ray projection of a calibration body for the first position on the movement trajectory in order to acquire a first measuring result for at least one feature of the calibration body; and
      comparing the first measuring result to a respective reference in order to determine an error measure;
   wherein the calibrator is configured to solve the system of equations in order to acquire the parameters to be calibrated;
   wherein the X-ray system comprises at least one robot or multi-element robot;
   wherein the robot or multi-element robot moves the radiation source, an object or the detector such that the radiation source, the object and/or the radiation detector are movable in dependence on machine parameters for driving the robot; and
   wherein the kinematic parameters of the set of kinematic parameters describe the kinematic model of the entire system comprising at least the robot or multi-element robot, wherein the kinematic parameters comprise non-variable kinematic parameters comprising a leg length of a component of the robot or multi-element robot, and variable kinematic parameters comprising the machine parameters which describe the movement or position of the respective joint of the robot or multi-element robot.

21. The apparatus in accordance with claim 20, the apparatus comprising an interface for controlling the X-ray system and/or for controlling robots of the X-ray system.

22. An X-ray system comprising a radiation source and an X-ray source, and an apparatus in accordance with claim 20.

23. The X-ray system in accordance with claim 22, wherein the X-ray system comprises a first robot by means of which the radiation source is movable, and a second robot by means of which the radiation detector is movable.

24. A method for an X-ray-based calibration and adjustment of axis systems by means of an X-ray system comprising a radiation source and a radiation detector, wherein the X-ray system comprises two multi-element robots; wherein a first one of the two robots moves the radiation source and the second one of the two robots moves the radiation detector so that the radiation source and/or the radiation detector is/are movable in dependence on machine parameters for driving the robots, comprising:
   establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations;
   setting the starting values for the parameters to be calibrated; and
   calibrating comprising:
      establishing an X-ray projection of a calibration body for the first position on the movement trajectory in order to acquire a first measuring result for at least one feature of the calibration body; and
      comparing the first measuring result to a respective reference in order to determine an error measure; and
      solving the system of equations in order to determine the parameters to be calibrated;
   wherein the parameters to be calibrated describe an offset of the radiation source relative to the robot, described in the kinematic model, which moves the radiation source; and/or
   wherein the parameters to be calibrated describe an offset between the X-ray detector and the kinematic model of the robot which moves the radiation detector.

25. An apparatus for an X-ray-based calibration and adjustment of axis systems by means of an X-ray system comprising a radiation source and a radiation detector, wherein the X-ray system comprises two multi-element robots; wherein a first one of the two robots moves the radiation source and the second one of the two robots moves the radiation detector so that the radiation source and/or the radiation detector is/are movable in dependence on machine parameters for driving the robots, comprising:
- a calculating unit for establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations;
- a calibrator configured, based on fixed starting values for the parameters to be calibrated, to:
  - establish an X-ray projection of a calibration body for the first position on the movement trajectory in order to acquire a first measuring result for at least one feature of the calibration body; and
  - compare the first measuring result to a respective reference in order to determine an error measure;
  - wherein the calibrator is configured to solve the system of equations in order to acquire the parameters to be calibrated;
- wherein the parameters to be calibrated describe an offset of the radiation source relative to the robot, described in the kinematic model, which moves the radiation source; and/or
- wherein the parameters to be calibrated describe an offset between the X-ray detector and the kinematic model of the robot which moves the radiation detector.

26. A non-transitory digital storage medium having stored thereon a computer program for performing a method for an X-ray-based calibration and adjustment of axis systems by means of an X-ray system comprising a radiation source and a radiation detector, wherein the X-ray system comprises two multi-element robots; wherein a first one of the two robots moves the radiation source and the second one of the two robots moves the radiation detector so that the radiation source and/or the radiation detector is/are movable in dependence on machine parameters for driving the robots, comprising:
- establishing a kinematic model of the X-ray system with all the kinematic relations for a first position on the movement trajectory and describing the same using a first set of kinematic parameters and using parameters to be calibrated, wherein the first set of kinematic parameters and the parameters to be calibrated define a first equation of a system of equations;
- setting the starting values for the parameters to be calibrated; and
- calibrating comprising:
  - establishing an X-ray projection of a calibration body for the first position on the movement trajectory in order to acquire a first measuring result for at least one feature of the calibration body; and
  - comparing the first measuring result to a respective reference in order to determine an error measure; and
  - solving the system of equations in order to determine the parameters to be calibrated;
- wherein the parameters to be calibrated describe an offset of the radiation source relative to the robot, described in the kinematic model, which moves the radiation source; and/or
- wherein the parameters to be calibrated describe an offset between the X-ray detector and the kinematic model of the robot which moves the radiation detector, when said computer program is run by a computer.

\* \* \* \* \*